US012082978B2

(12) United States Patent
Jones et al.

(10) Patent No.: US 12,082,978 B2
(45) Date of Patent: Sep. 10, 2024

(54) TRAJECTORY GUIDE WITH DUAL GIMBAL DRIVE ARRANGEMENT

(71) Applicant: Advanced Neuromodulation Systems, Inc., Plano, TX (US)

(72) Inventors: Robert E. Jones, McKinney, TX (US); Galen L. Smith, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 199 days.

(21) Appl. No.: 17/688,868

(22) Filed: Mar. 7, 2022

(65) Prior Publication Data
US 2022/0192775 A1    Jun. 23, 2022

Related U.S. Application Data

(62) Division of application No. 16/265,704, filed on Feb. 1, 2019, now Pat. No. 11,298,204.

(51) Int. Cl.
*A61B 90/11* (2016.01)
*A61B 90/50* (2016.01)
(Continued)

(52) U.S. Cl.
CPC .............. *A61B 90/11* (2016.02); *A61B 90/50* (2016.02); *A61B 1/3135* (2013.01); *A61B 10/04* (2013.01);
(Continued)

(58) Field of Classification Search
CPC .......... A61B 90/11; A61B 2018/00446; A61B 2090/1063; A61N 1/0534
See application file for complete search history.

(56) References Cited

U.S. PATENT DOCUMENTS

| 2,948,168 A | 8/1960 | McCormick |
| 4,955,891 A | 9/1990 | Carol |

(Continued)

FOREIGN PATENT DOCUMENTS

| CN | 105232126 A | 1/2016 |
| GB | 922007 A | 3/1963 |

(Continued)

OTHER PUBLICATIONS

European Patent Office, Communication, Extended European Search Report for European Patent Application No. 20748024.5, dated Oct. 25, 2022, 10 pages.

(Continued)

*Primary Examiner* — Martin T Ton
(74) *Attorney, Agent, or Firm* — Norton Rose Fulbright US LLP

(57) ABSTRACT

A trajectory guiding apparatus and one or more methods associated therewith for facilitating precision-guided alignment and implantation of a DBS therapy device in a patient. A pivotally rotatable stage is pivotally coupled to a base support and a vertical support operative to support a slider assembly arranged to accommodate an instrumentation column (IC) containing the therapy device. A first gimbal drive is disposed between the pivotally rotatable stage and the base support, wherein the first gimbal drive is actuatable to cause a first pivotal motion of the slider assembly including the IC, the first pivotal motion defined along a first arcuate path pivoted around a first pivotal axis. A second gimbal drive is disposed between the pivotally rotatable stage and the vertical support, wherein the second gimbal drive is actuatable to cause a second pivotal motion of the slider assembly including the IC, the second pivotal motion defined along a second arcuate path pivoted around a second pivotal axis perpendicular to the first pivotal axis.

7 Claims, 11 Drawing Sheets

(51) Int. Cl.

| | | |
|---|---|---|
| A61B 1/313 | (2006.01) | |
| A61B 10/04 | (2006.01) | |
| A61B 17/00 | (2006.01) | |
| A61B 17/34 | (2006.01) | |
| A61B 18/00 | (2006.01) | |
| A61B 90/10 | (2016.01) | |
| A61M 25/01 | (2006.01) | |
| A61N 1/05 | (2006.01) | |

(52) U.S. Cl.
CPC .......... *A61B 2017/00911* (2013.01); *A61B 2017/3407* (2013.01); *A61B 2017/3409* (2013.01); *A61B 2018/00446* (2013.01); *A61B 2018/00577* (2013.01); *A61B 2090/103* (2016.02); *A61B 2217/005* (2013.01); *A61B 2217/007* (2013.01); *A61M 25/01* (2013.01); *A61N 1/0534* (2013.01)

(56) References Cited

U.S. PATENT DOCUMENTS

| | | | |
|---|---|---|---|
| 5,094,243 A * | 3/1992 | Puy | G10K 11/004 |
| | | | 600/459 |
| 5,154,723 A | 10/1992 | Kubota et al. | |
| 6,491,699 B1 | 12/2002 | Henderson et al. | |
| 7,736,371 B2 | 6/2010 | Schoepp | |
| 7,744,606 B2 | 6/2010 | Miller et al. | |
| 7,949,410 B2 | 5/2011 | Rodriguez | |
| 8,463,387 B2 | 6/2013 | De Ridder | |
| 8,747,418 B2 | 6/2014 | Qureshi et al. | |
| 9,192,446 B2 | 11/2015 | Piferi et al. | |
| 9,232,977 B1 | 1/2016 | Rehman et al. | |
| 9,370,653 B2 | 6/2016 | Sefkow et al. | |
| 10,456,201 B1 | 10/2019 | Solar et al. | |
| 2001/0053879 A1 | 12/2001 | Mills et al. | |
| 2006/0122627 A1 | 6/2006 | Miller et al. | |
| 2008/0306375 A1 | 12/2008 | Sayler et al. | |
| 2009/0112084 A1 * | 4/2009 | Piferi | A61N 1/0529 |
| | | | 600/421 |
| 2009/0131783 A1 | 5/2009 | Jenkins et al. | |
| 2010/0042111 A1 | 2/2010 | Qureshi et al. | |
| 2011/0190787 A1 | 8/2011 | Sahni | |
| 2011/0237881 A1 | 9/2011 | Kunz | |
| 2014/0024927 A1 | 1/2014 | Piferi | |
| 2015/0031982 A1 | 1/2015 | Piferi et al. | |
| 2016/0256233 A1 * | 9/2016 | Pandey | A61B 5/055 |
| 2017/0202631 A1 * | 7/2017 | Piferi | A61B 90/11 |
| 2017/0311978 A1 | 11/2017 | Chieng | |
| 2018/0008821 A1 | 1/2018 | Gonzalez et al. | |
| 2020/0246099 A1 | 8/2020 | Jones et al. | |
| 2020/0246101 A1 | 8/2020 | Jones et al. | |
| 2020/0390465 A1 * | 12/2020 | Sánchez López | A61B 90/39 |

FOREIGN PATENT DOCUMENTS

| | | |
|---|---|---|
| WO | WO-2016064282 A1 | 4/2016 |
| WO | WO-2019157070 A1 | 8/2019 |

OTHER PUBLICATIONS

ISA/US, Written Opinion and International Search Report, Application No. PCT/US2020/015650, May 21, 2020, 15 pgs.

ISA/US, Written Opinion and International Search Report, Application No. PCT/US2020/015702, Apr. 1, 2020, 13 pgs.

ISA/US, Written Opinion and International Search Report, Application No. PCT/US2020/015849, Jun. 9, 2020, 16 pgs.

* cited by examiner

TRAJECTORY GUIDE WITH DUAL GIMBAL DRIVE ARRANGEMENT

CROSS-REFERENCE TO RELATED APPLICATION(S)

This application is a Divisional of U.S. application Ser. No. 16/265,704, titled "TRAJECTORY GUIDE WITH DUAL GIMBAL DRIVE ARRANGEMENT," filed on Feb. 1, 2019 and now issued as U.S. Pat. No. 11,298,204 on Apr. 12, 2022, which is hereby incorporated by reference in its entirety. This application also discloses subject matter that is related to the subject matter of the following U.S. patent application(s): (i) "TRAJECTORY GUIDE WITH DOUBLE X-Y SLIDING TABLES", application Ser. No. 16/265,674, now U.S. Pat. No. 11,406,470, filed Feb. 1, 2019, in the name(s) of Galen L. Smith and Robert Jones; and (ii) "TRAJECTORY GUIDE WITH DUAL ARC ARRANGEMENT", application Ser. No. 16/265,737, now U.S. Pat. No. 11,364,086, filed Feb. 1, 2019, in the name(s) of Galen L. Smith and Robert Jones; each of which is hereby incorporated by reference in its entirety.

TECHNICAL FIELD

The present disclosure generally relates to surgical platforms used in medical device placement. More particularly, and not by way of any limitation, the present disclosure is directed to a trajectory guide and associated method for providing trajectory alignment and implantation of a therapy device in a patient.

BACKGROUND

The use electrical stimulation for treating neurological disease, including such disorders as movement disorders including Parkinson's disease, essential tremor, dystonia, chronic pain, and the like has been widely discussed in the literature. In many instances, the preferred objective is to modulate neuronal activity in certain known target areas of the central nervous system of a patient. Electrical stimulation permits such modulation of the target neural structures, e.g., various regions in the patient's brain, and, equally importantly, does not require the destruction of nervous tissue. Efforts have also been underway to treat psychiatric disorders with peripheral/cranial nerve stimulation such as, e.g., depression, compulsive eating disorders, etc.

Deep brain stimulation (DBS) refers to the delivery of electrical pulses into one or several specific sites within the brain of a patient to treat various disorders. For example, DBS has been proposed as a clinical technique for treatment of chronic pain, essential tremor, Parkinson's disease (PD), dystonia, epilepsy, depression, obsessive-compulsive disorder, and other disorders.

Stereotactic neurosurgery is a field of neurosurgery in which an implantable medical device is advanced through a burr hole in the cranium of a patient to a target region of interest by means of a mechanical device attached to the skull with aiming based on pre-operative and/or intraoperative imaging. For the past decade or so, the field has been advancing from using large, classical metal frames (e.g., "center-of-arc" systems), which typically encompass the entire head of a patient, to the attachment of small platforms placed only over an entry site (commonly referred to as "frameless" or "microframe" technologies).

Whereas advances in stereotactic surgical instrumentation and devices continue to grow apace, several lacunae remain, thereby requiring further innovation as will be set forth hereinbelow.

SUMMARY

Embodiments set forth herein are directed to a trajectory guiding apparatus and one or more methods associated therewith for facilitating precision-guided alignment and implantation of a therapy device in a patient while providing reduced patient discomfort, ease of surgical access, and other benefits that will become apparent from the description herein.

In one aspect, an example trajectory guiding apparatus according to an embodiment of the present patent disclosure comprises, inter alia, a base support comprising a frame portion and a first pivot housing portion, the frame portion having a first aperture sized to surround a burr hole opening in a patient's cranium and the frame portion configured for fastening the base support to the cranium, wherein the base support further includes a first gimbal coupler. A pivotally rotatable stage is pivotally coupled to the base support at the first pivot housing portion defining a first pivotal axis, wherein the pivotally rotatable stage includes a stage portion and a second pivot housing portion, the stage portion having a second gimbal coupler and a third gimbal coupler. A vertical support comprises a bottom end and a top end, wherein the bottom end includes a fourth gimbal coupler and is pivotally coupled to the pivotally rotatable stage at the second pivot housing portion defining a second pivotal axis. Preferably, the first and second pivotal axes are perpendicular to each other. A slider assembly is preferably removably coupled to the vertical support at the top end, the slider assembly including a second aperture, e.g., at least as large as the first aperture in the frame portion, and configured to accommodate an instrumentation column having a columnar passage therethrough and coupled to a drive assembly for advancing a distal end of an elongate medical device through the columnar passage of the instrumentation column. In one arrangement, a first gimbal drive is coupled or otherwise articulated between the first gimbal coupler of the base support and the second gimbal coupler of the stage portion of the pivotally rotatable stage, wherein the first gimbal drive is actuatable to cause a first pivotal motion of the slider assembly including the instrumentation column, the first pivotal motion defined along a first arcuate path pivoted around the first pivotal axis. A second gimbal drive is coupled or otherwise articulated between the third gimbal coupler of the stage portion of the pivotally rotatable stage and the fourth gimbal coupler of the bottom end of the vertical support, the second gimbal drive actuatable to cause a second pivotal motion of the slider assembly including the instrumentation column, the second pivotal motion defined along a second arcuate path pivoted around the second pivotal axis, the first and second arcuate paths being perpendicular to each other. In one arrangement, the first and second gimbal drives are independently actuatable such that after aligning a distal end of the instrumentation column with a target entry point in the burr hole using the slider assembly, an axial angle of the instrumentation column is operative to be adjusted by actuating at least one of the first and second gimbal drives while maintaining the alignment of the distal end of the instrumentation column with the target entry point in the burr hole. In other words, a polar and/or an azimuthal angular separation between the longitudinal axis of the instrumentation column and the perpendicular axis of the burr hole plane may be varied while a target entry point within the burr hole is held relatively constant (or "gimbaled").

In one embodiment, the slider assembly of an exemplary trajectory guiding apparatus comprises a coupling portion having a coupling mechanism configured for facilitating removable coupling with the top end of the vertical support, the coupling portion laterally extending to form a platform portion having a grooved surface surrounding the second aperture therein. A lower plate is slidably engaged with the grooved surface of the platform portion, the lower plate having a third aperture, e.g., at most as large as the second aperture in an example embodiment. An upper plate is slidably engaged with the lower plate and configured to rigidly couple to the instrumentation column, wherein the lower plate is operative to slide along a first axis and the upper plate is operative to slide along a second axis, the first and second axes orthogonal to each other and disposed along a translational motion plane substantially parallel relative to a burr hole plane that is co-planar with the burr hole.

In one example embodiment, the first and second gimbal drives of an exemplary trajectory guiding apparatus each comprise a respective angled screw drive having a threaded shaft. In a further variation, an angular range of the first pivotal motion of an example trajectory guiding apparatus may be determined by at least one of an angle of the threaded shaft of the first gimbal drive relative to the burr hole plane and a length of the threaded shaft of the first gimbal drive. In similar fashion, an angular range of the second pivotal motion an example trajectory guiding apparatus may be determined by at least one of an angle of the threaded shaft of the second gimbal drive relative to the burr hole plane and a length of the threaded shaft of the second gimbal drive.

In another aspect, an example method according to an embodiment of the present patent disclosure for implanting an elongate medical device into a patient's brain comprises, inter alia, obtaining trajectory path information regarding at least one of a path entry point, a target location, a trajectory path and an entry angle with respect to implanting the elongate medical device through the patient's cranium, the elongate medical device configured to provide a particular therapy; creating a burr hole in the cranium around the path entry point; attaching a trajectory guiding apparatus including an instrumentation column (IC) assembly that contains the elongate medical device, the trajectory guiding apparatus having a base support member configured to be secured to the cranium and surround the burr hole in a close proximity; adjusting a translational/planar movement by actuating an X-Y slider table of the trajectory guiding apparatus to align the IC assembly to the path entry point in the burr hole; adjusting a pivotal rotational movement by actuating at least one of a first gimbal drive and a second gimbal drive of the trajectory guiding apparatus to align an axial angle of the IC assembly with the entry angle; and advancing the elongate medical device using a drive assembly associated with the IC assembly until the target location is reached.

In one variation, an embodiment of the method may further comprise continuing to guide the elongate medical device along the trajectory path as the elongate medical device is advanced in the patient's brain; and if a path deviation is determined, obtained or otherwise indicated, applying at least one of a translational adjustment and/or a rotational/angular adjustment by actuating at least one of the X-Y table and/or one or both gimbal drives to realign the elongate medical device with the trajectory path.

In one arrangement, an embodiment of the elongate medical device may comprise at least one of a DBS lead comprising a plurality of electrodes at a distal end, a biopsy instrumentation device, a catheter insertion device, an injection and aspiration device, a neurological endoscopy device, a microelectrode recording (MER) device, a macro stimulation device, a cannula device, a neurological ablation device, and a brain lesioning device, and the like.

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
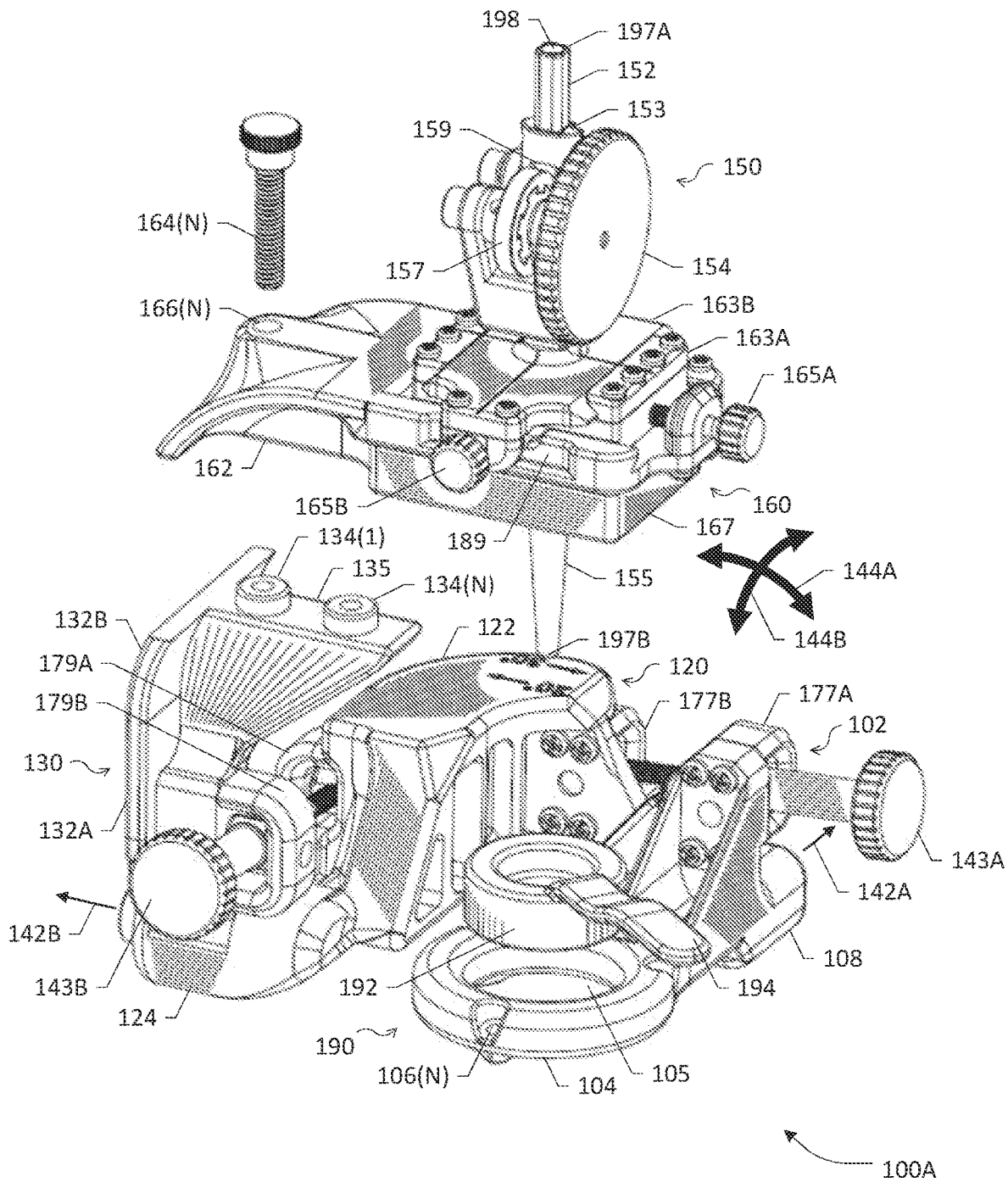
FIG. 1A depicts a 3-dimensional (3D) partially disassembled view of an example trajectory guide apparatus including a dual gimbal drive arrangement for effectuating independent translational and pivotal movement of an instrumentation column (IC) according to an embodiment of the present patent application.

In the description herein for embodiments of the present disclosure, numerous specific details are provided, such as examples of mechanical elements, devices, components and/or methods, etc., to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an element, component or module may be configured to perform a function if the element may be constructed for performing or otherwise structurally arranged to perform that function.

Further, while reference is made to the accompanying drawing Figures that form a part hereof with respect to illustrative embodiments, it is to be understood that other embodiments, which may not be described and/or illustrated herein, are certainly contemplated. To the extent any headings, sub-titles, captions, banners, etc. are provided in the present disclosure, it should be understood that they are provided only for the convenience of the reader and not be used to limit the meaning of any text that follows the heading, sub-title, banner or caption unless so specified. Moreover, all numbers expressing quantities, and all terms expressing direction/orientation (e.g., vertical, horizontal, parallel, perpendicular, etc.) in the specification and claims are to be understood as being modifiable in all instances by the terms "about," "approximately," or terms of similar import, which may represent commonly known allowances or deviations from the quantities and directions being described unless otherwise indicated.

Referring now to the drawings wherein like or similar elements are designated with identical reference numerals throughout the several views, and wherein the various elements depicted are not necessarily drawn to scale, and referring to FIG. 1A in particular, depicted therein is a 3-dimensional (3D) partially disassembled view of an example trajectory guide apparatus 100A including a dual gimbal drive arrangement coupled with an X-Y slider assembly for effectuating independent translational and pivotal/rotational movement and/or adjustment of a tubular instrumentation column (IC) or assembly 150 according to an embodiment of the present patent application. A base support 102 comprising a frame portion 104 and a first pivot housing portion 108 is provided as a foundation configured for securely fastening the trajectory guide apparatus 100A to a patient's cranium, wherein the frame portion 104 is provided with a first aperture 105 roughly sized to surround a burr hole opening in the patient's cranium. In one arrangement, the burr hole may have been created based on stereotactic information comprising, e.g., predetermined target location in the patient's brain, entry point on the skull, entry angle, trajectory, etc., using any known image scanning and acquisition technology in conjunction with a suitable stereotactic apparatus configuration. In one arrangement, the frame portion 104 of base support 102 preferably comprises an annular structure having a circular orifice forming the first aperture 105, the circular orifice optimally sized to surround the burr hole in a close proximity. Further, in one arrangement, the frame portion 104 may be provided with a minimum number of holes (e.g., 2, 3 or more), e.g., holes 106(N), for securely fastening the base support 102 to the cranium with surgical screws, which may be sized and positioned in the frame portion 104 such that a firm attachment to the patient's skull can be achieved that can withstand various movements, e.g., torquing, bumping, or other potentially dislodging and/or disorienting forces that may be encountered while the patient is moved around within the surgical facility, while causing only a minimal amount of discomfort to the patient during the procedure. Skilled artisans will recognize that the frame portion 104 may also be comprised of different shapes (e.g., oval, obround, elliptical, square, hexagonal, octagonal, etc.) having suitably shaped apertures and provided with a varying minimum number of fasteners in other arrangements for purposes of an embodiment of the present patent disclosure.

A pivotally rotatable stage 120 is pivotally coupled to the base support 102 at the first pivot housing portion 108, wherein the pivotally rotatable stage 120 and the first pivot housing portion 108 are articulated for defining a first pivotal axis 142A. In one example arrangement, the pivotally rotatable stage 120 includes a stage portion 122 and a second pivot housing portion 124. A vertical support 130 having a bottom end or terminus 132A and a top end or terminus 132B is coupled or otherwise articulated to the pivotally rotatable stage 120 such that the bottom end 132A is pivotally coupled to the second pivot housing portion 124 for defining a second pivotal axis 142B thereat, wherein the first and second pivot axes 142A, 142B are perpendicular to each other. A slider assembly 160 is preferably removably coupled to the top terminus 132B of the vertical support 130.

In one arrangement, the slider assembly 160 includes a second aperture 189 that is substantially the same size as or at least as large as the first aperture 105 of the frame portion 104, and preferably configured to accommodate and allow the movement of the IC assembly 150 having a tubular shaft 152 with a columnar passage 198 therethough for advancing a distal end of an elongate medical device.

In one arrangement, one or more fastening mechanisms 164(N) may be utilized for coupling the slider assembly 160 in a "semi-permanent" manner to the top terminus 132B for facilitating removable coupling therebetween. Skilled artisans will recognize that such fastening mechanisms 164(N) may comprise, e.g., screws, bolts, pins, etc., that may be driven through or otherwise mechanically engaged with corresponding threaded or unthreaded holes 166(N) provided in a coupling portion 162 of the slider assembly 160, which may be mated or otherwise aligned with matching holes or apertures 134(1)-134(N) provided in a horizontal support member 135 extending from the top terminus 132B of the vertical support 130.

In one arrangement, the base support 102, stage portion 122 and bottom end 132A are each provided with or otherwise include a respective gimbal coupler, bracket, brace, etc. for purposes of an embodiment of the present patent application. By way of illustration, the base support 102 is provided with or otherwise articulated to a first gimbal coupler 177A, the stage portion 122 is provided with or otherwise articulated to a second gimbal coupler 177B and a third gimbal coupler 179A, and the bottom end 132A is provided with or otherwise articulated to a fourth gimbal coupler 179B. Preferably, the first and second gimbal couplers 177A and 177B are aligned in a first direction whereas the third and fourth gimbal couplers 179A and 179B are aligned in a second direction perpendicular to the first direction.

A first gimbal drive 143A is coupled, articulated or otherwise disposed between the first gimbal coupler 177A of the base support 102 and the second gimbal coupler 177B of the stage portion 122 of the pivotally rotatable stage 120, wherein the first gimbal drive 143A is actuatable to cause a first pivotal motion of the slider assembly 160 including the IC assembly 150 such that the first pivotal motion is defined along a first arcuate path or curvilinear path 144A pivoted around the first pivotal axis 142A. In similar fashion, a second gimbal drive 143B is coupled, articulated or otherwise disposed between the third gimbal coupler 179A of the stage portion 122 of the pivotally rotatable stage 120 and the fourth gimbal coupler 179B of the bottom end 132A of the vertical support 130, wherein the second gimbal drive 143B is actuatable to cause a second pivotal motion of the slider assembly 160 including the IC assembly 150 such that the second pivotal motion is defined along a second arcuate or curvilinear path 144B pivoted around the second pivotal axis 142B. As will be further explained below, the first and second arcuate paths 144A, 144B are perpendicular to each other in a 3D spherical space, or at least a portion thereof defined by the range of the respective angular movements allowed for the IC assembly 150. Preferably, the first and second gimbal drives 143A, 143B are independently actuatable such that after aligning a distal end of the IC assembly 150 (or, analogously, the shaft 152 of the IC assembly 150) with a target entry point in the burr hole using the slider assembly 160, an axial angle of the IC assembly 150 is operative to be adjusted by actuating at least one of the first and second gimbal drives 143A, 143B while maintaining the alignment of the distal end of the instrumentation column with the target entry point in the burr hole.

Figure 1B:
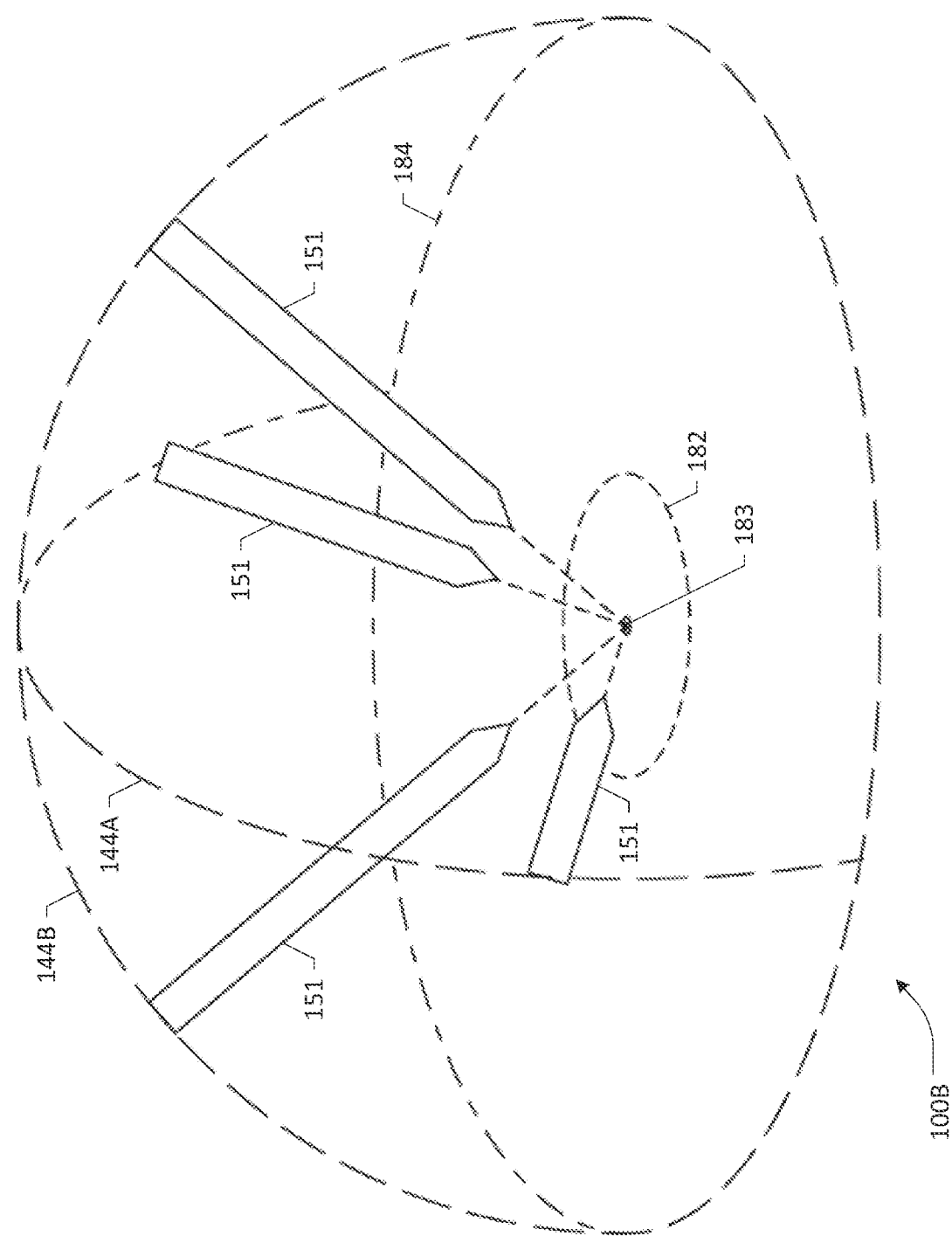
FIG. 1B depicts a 3D representation of a semispherical space illustrating orthogonal arcuate paths of an IC assembly that may be effectuated by the example trajectory guide apparatus of FIG. 1A according to an embodiment of the present patent application.
Figure 3:
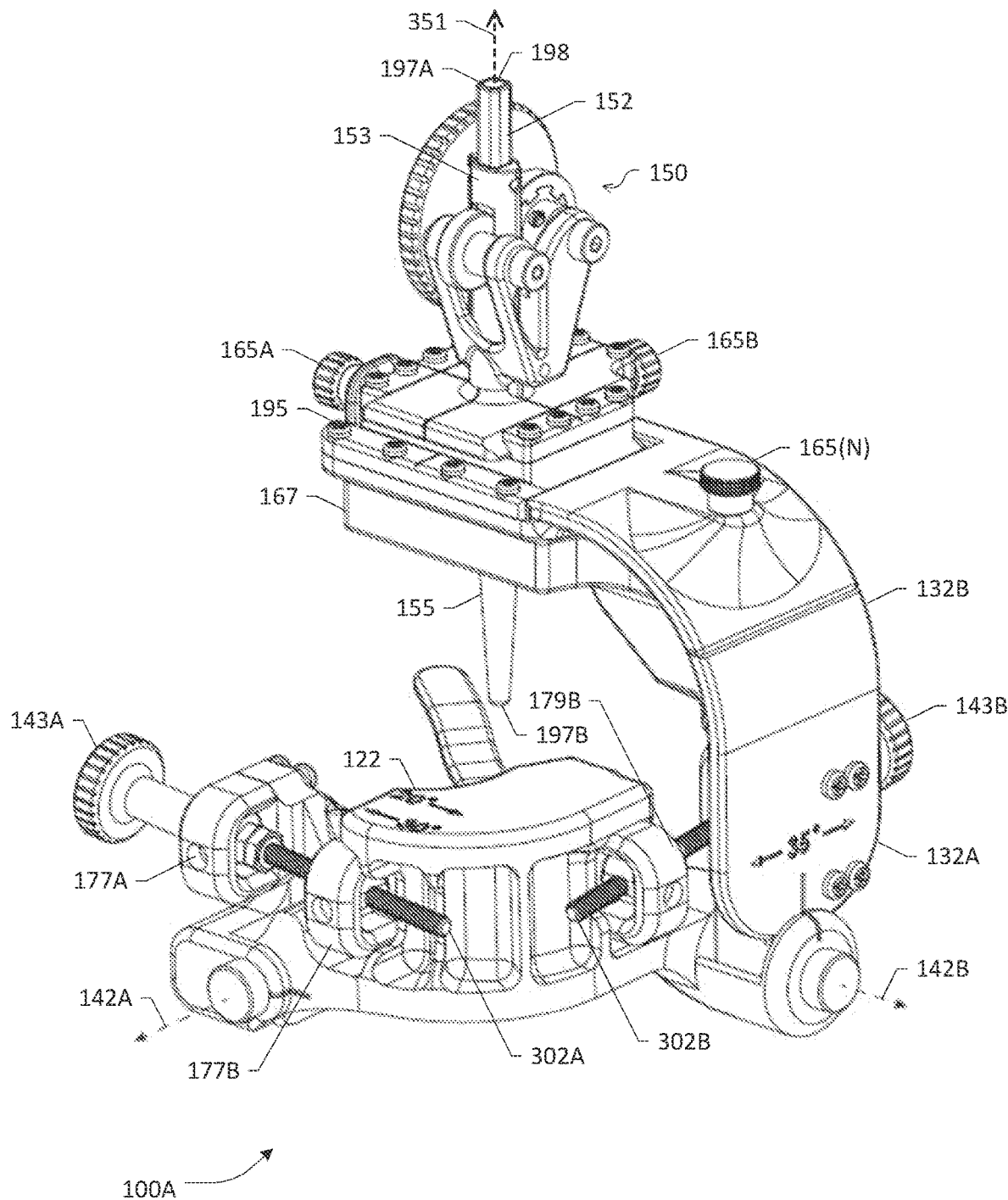
FIG. 3 depicts another 3D isometric view of the example trajectory guide apparatus of FIG. 1A.

For purposes of further illustration, reference is taken to FIG. 1B wherein reference numeral 151 refers to a representation of the tubular shaft 152 of IC assembly 150 shown in FIG. 1A, wherein shaft 152 is provided with a proximate end 197A and a distal end 197B, each end having an orifice for allowing the passage of an elongate medical device therethrough in the columnar passage 198. As further exemplified in FIG. 1A, shaft 152 may have a varying shape and/or thickness lengthwise. For example, a portion 155 extending below the slider assembly 160 may be formed as a tapered tube or elongated cylindrical structure whereas a portion 153 above the slider assembly 160 may shaped differently to facilitate attachment with a drive assembly 154 as will be set forth further below. Regardless of the lengthwise variation in the shape of the shaft 152, a vertical or longitudinal axis 351 of the IC/shaft 150/152 may be defined (as illustrated in FIG. 3 described further below) that may need to be aligned to a target path's entry angle relative to a burr hole 182 and a target entry point 183 therein, which may be defined as being co-planar with a plane 184 (e.g., burr hole plane). In general, the burr hole plane 184 defines an X-Y reference plane with respect to the two perpendicular arcuate paths 144A and 144B that may be traced by the IC assembly 150 when actuated by respective gimbal drives 143A and 143B. It will be appreciated that by actuating the first gimbal drive 143A, the pivotally rotatable stage 120, the slider assembly 160 including the IC assembly 150 as well as the vertical support 130 coupled thereto are pivotally rotated along the first arcuate path 144A, which may referred to as a polar arcuate path disposed on the Z-Y plane of a 3D Cartesian coordinate system relative to the burr hole plane 184, wherein the X-axis is aligned to the first pivotal axis 142A of the base support 102. Likewise, by actuating the second gimbal drive 143B, the slider assembly 160 including the IC assembly 150 as well as the vertical support 130 coupled thereto are pivotally rotated around the second pivotal axis 142B (aligned to the Y-axis) for tracing a curved movement along the arcuate path 144B, which may referred to as an azimuthal arcuate path disposed on the Z-X plane. Accordingly, in an example 3D semispherical space 100B, different angular positions along the first arcuate path 144A determine or otherwise indicate the "polar" angle of the shaft representation 151, whose range on the Z-Y plane may be symmetrical or asymmetrical with respect to the Z-axis defined to align with a vertical axis passing through the target entry point 183 and perpendicular to the burr hole plane 184. In similar fashion, different angular positions along the second arcuate path 144B determine or otherwise indicate the "azimuthal" angle of the shaft representation 151, whose range on the Z-X plane may be symmetrical or asymmetrical with respect to the Z-axis aligned to the vertical axis passing through the target entry point 183 and perpendicular to the burr hole plane 184. As one skilled in the art will appreciate, different angular ranges may be provided for each quadrant of the first and second arcuate paths 144A and 144B depending on, e.g., how much axial variation is to be accommodated with respect to a target trajectory path's entry angle for a particular therapy application.

For purposes of the present patent application, remaining descriptive portions of the trajectory guiding apparatus 100A will be set forth below by taking reference to FIG. 2 to FIG. 6 in conjunction with FIGS. 1A-1B, wherein the trajectory guiding apparatus 100A is depicted in different views, with the foregoing description being applicable, mutatis mutandis, as necessary.

Figure 2:
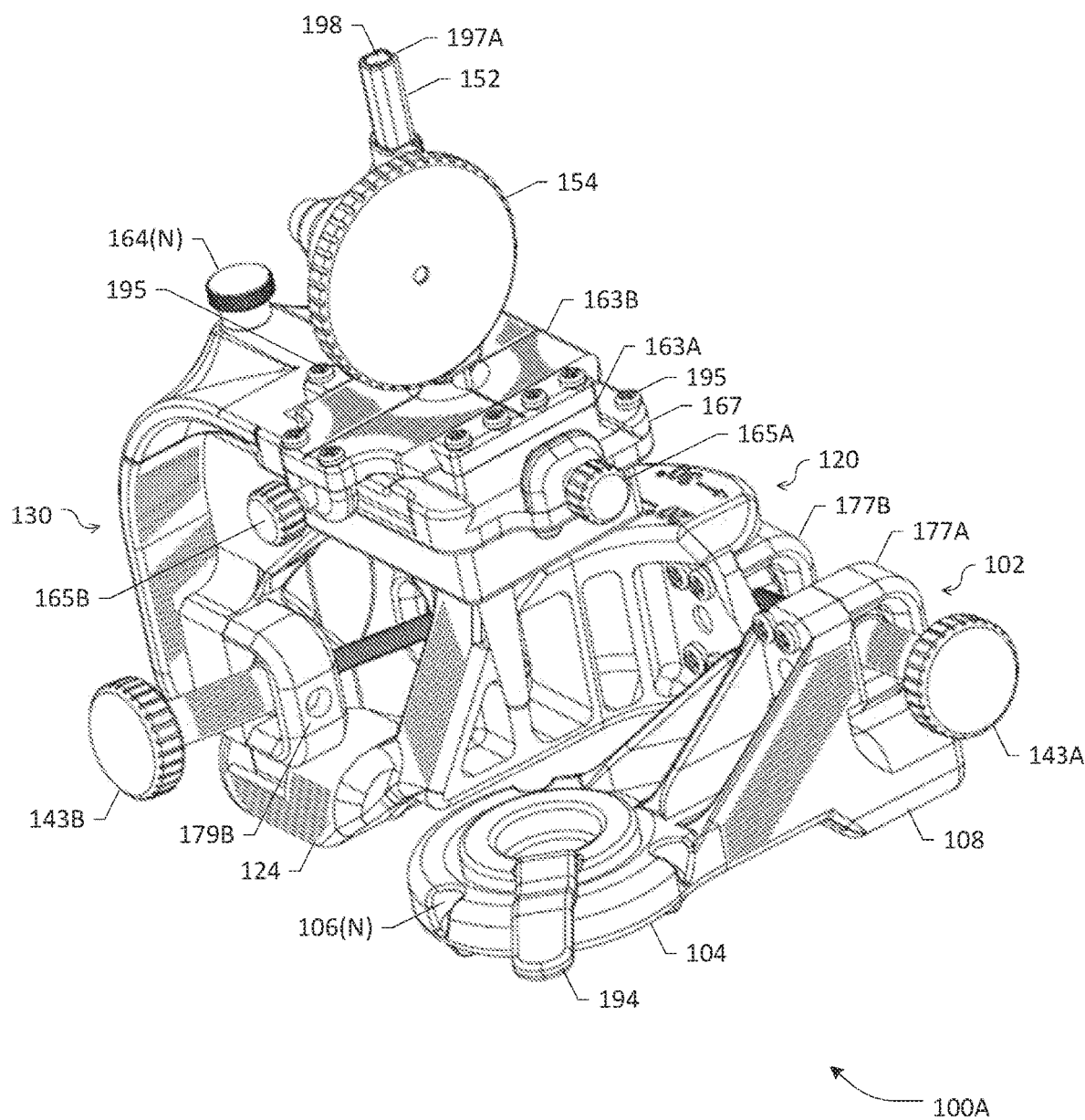
FIG. 2 depicts a 3D isometric view of the example trajectory guide apparatus of FIG. 1A.
Figure 4:
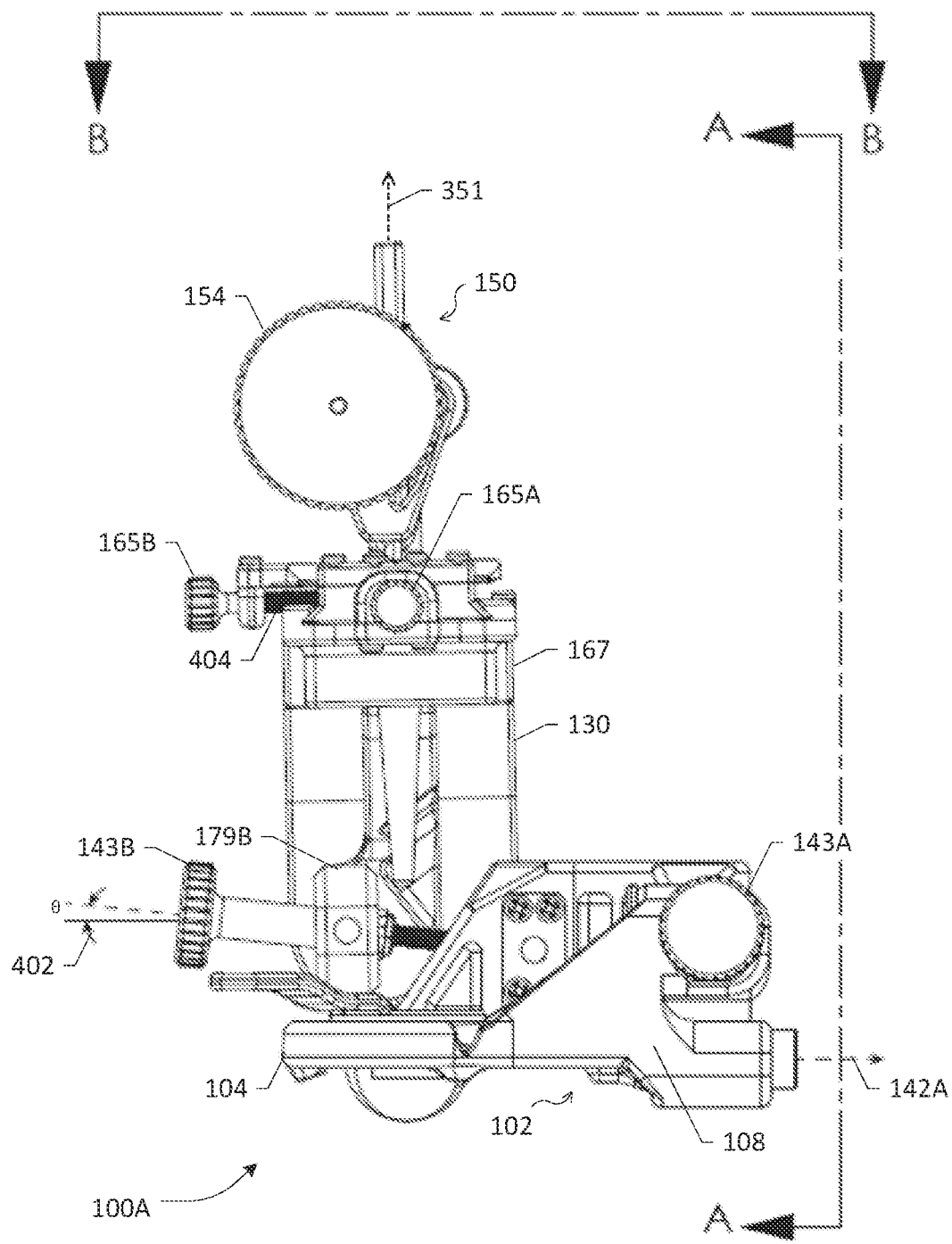
FIG. 4 depicts a front view of the example trajectory guide apparatus of FIG. 1A.
Figure 5A:
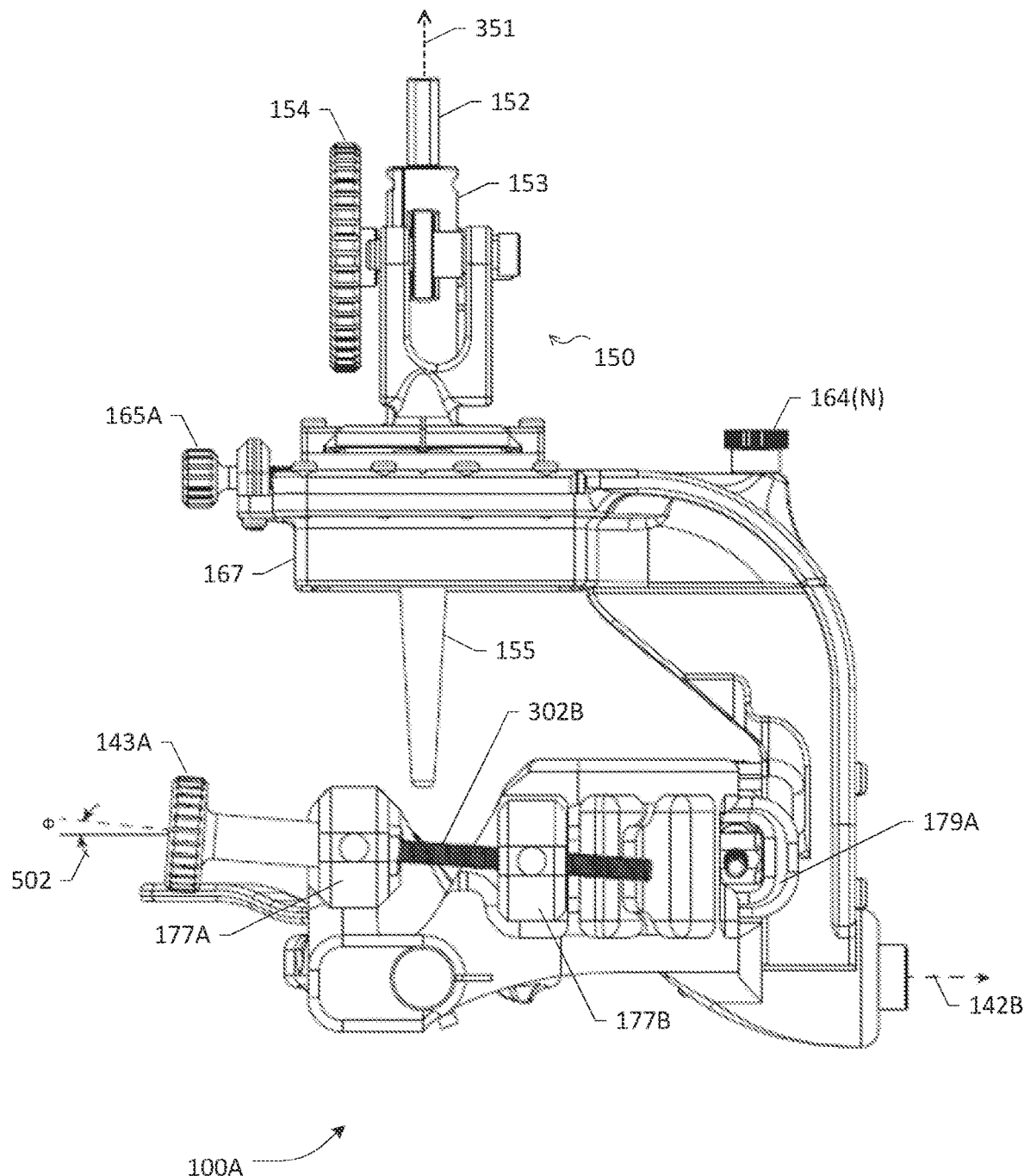
FIG. 5A depicts a side view of the example trajectory guide apparatus of FIG. 1A viewed from the A-A plane shown in FIG. 4.
Figure 5B:
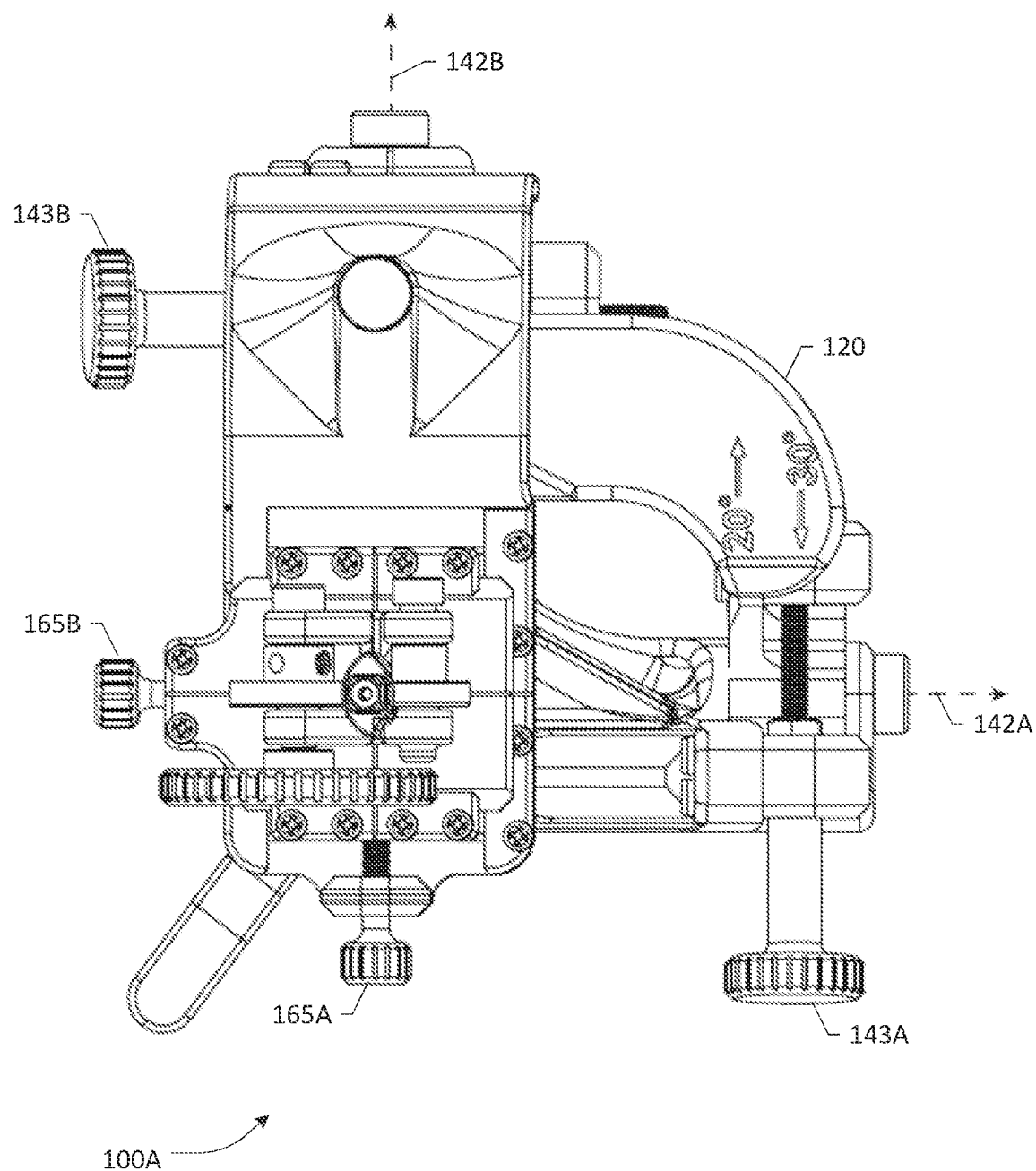
FIG. 5B depicts a top view of the example trajectory guide apparatus of FIG. 1A viewed from the B-B plane shown in FIG. 4.
Figure 6:
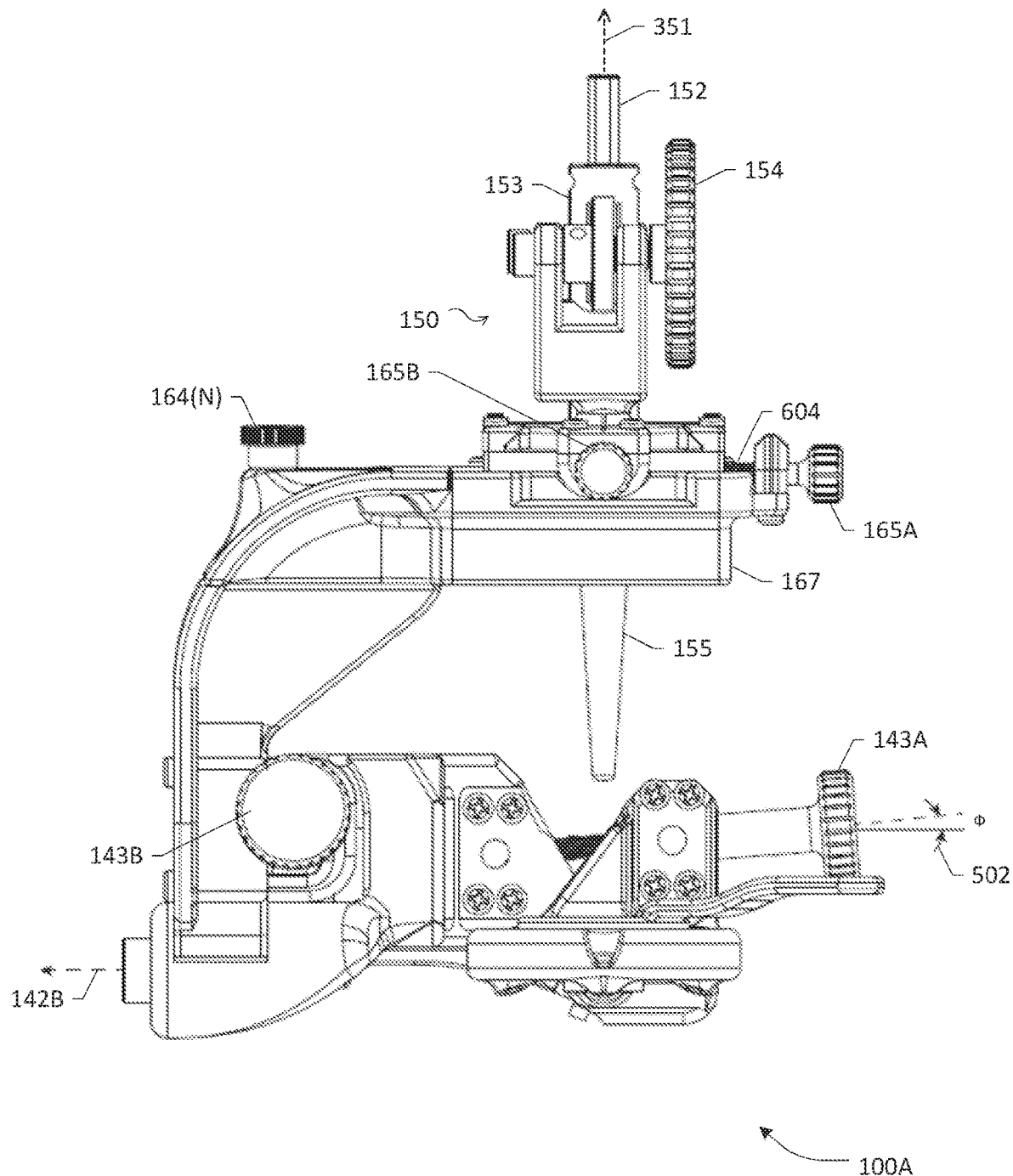
FIG. 6 depicts another side view of the example trajectory guide apparatus of FIG. 1A viewed from a direction opposite to the direction of the A-A plane shown in FIG. 4.

FIG. 2 depicts a 3D isometric view of the example trajectory guide apparatus 100A of FIG. 1A as assembled. FIG. 3 depicts another isometric view of the example trajectory guide apparatus 100A. FIG. 4 depicts a front view of the example trajectory guide apparatus 100A. FIG. 5A depicts a side view of the example trajectory guide apparatus 100A viewed from the A-A plane shown in FIG. 4. FIG. 5B depicts a top view of the example trajectory guide apparatus 100A viewed from the B-B plane shown in FIG. 4. FIG. 6 depicts another side view of the example trajectory guide apparatus 100A viewed from a direction opposite to the direction of the A-A plane shown in FIG. 4.

In one example embodiment, the slider assembly 160 of the trajectory guiding apparatus 100A may comprise a coupling portion 162 that extends laterally from a platform portion 167, wherein the coupling portion 162 may be configured to include one or more coupling or fastening mechanisms for facilitating removable coupling with the horizontal support member 135 extending from top end 132B of the vertical support 130. As set forth previously, such coupling mechanisms may include one or more screws, bolts, dowels, pins, etc., that may be engaged via corresponding holes, apertures, etc., in respective coupled elements 162, 135. Platform portion 167 may be provided with a grooved surface surrounding the second aperture 189 therein for supporting and slidably engaging a lower plate 163A, wherein the lower plate 163A may be provided with a third aperture that is preferably no larger than the second aperture 189. An upper plate 163B may be provided to be slidably engaged with the lower plate 163A and may be rigidly coupled to the shaft 152 of IC assembly 150. Preferably, the lower plate 163A is operative to slide along a first axis (e.g., substantially parallel to the second pivotal axis 142B) and the upper plate 163B is operative to slide along a second axis (e.g., substantially parallel to the first pivotal axis 142A), wherein the first and second axes are orthogonal to each other and disposed along a translational motion plane substantially parallel relative to the burr hole 182 and burr hole plane 184. Accordingly, it will be seen that lower and plates 163A, 163B slidably engaged or otherwise articulated with each other may form an X-Y slider table, wherein each plate may be actuated by a respective screw drive 165A, 165B, for effectuating translational motion of the IC assembly 150 (and shaft 152 thereof) on a translational motion plane substantially parallel to the burr hole 182. Such translation motion may comprise translational movement(s) in any cardinal direction along the translational motion plane (i.e., sideways or forward and/or backward directions). It will be realized that if the burr hole 182 is placed on top of the cranium such that the trajectory guide apparatus 100A is vertically affixed to the skull and aligned to the sagittal plane of the patient, the translational motion plane will be horizontal and perpendicular with respect thereto. On the other hand, if the burr hole 182 is placed on a side of the patient's cranium, the vertical axis of trajectory guide apparatus 100A will be angularly displaced from the sagittal or coronal plane of the cranium. Accordingly, the translational motion plane of the X-Y slider table 163A/163B will also be at an angle to the sagittal or coronal plane of the patient while being parallel to the burr hole plane 184.

In one arrangement, the first and second gimbal drives 143A and 143B each comprise a respective angled bolt screw drive having a threaded shaft 302A, 302B. As illustrated in the side views of the trajectory guiding apparatus 100A in FIGS. 5A and 6, an angle (4)) 502 may be configured for the first gimbal drive 143A by staggering the placement of first and second gimbal couplers 177A and 177B provided with the base support 102 and the stage portion 122 of the pivotally rotatable stage 120, respectively, (e.g., by providing off-center arrangement). Likewise, an angle (8) 402 may be configured for the second gimbal drive 143B as shown in FIG. 4, which depicts the front view of the trajectory guiding apparatus 100A, wherein the angle may be achieved by off-centering the placement of third and fourth gimbal couplers 179A and 179B provided with the stage portion 122 and the bottom end 132B of the vertical support 130, respectively. One skilled in the art will recognize that an angular range of the first pivotal motion of the IC assembly 150 along the first arcuate path 144A (i.e., the polar angle) may be determined by and/or dependent on a number of factors such as, e.g., at least one of the angle of the threaded shaft of the first gimbal drive relative to the burr hole plane (e.g., angle 502) and a length of the threaded shaft 302A of the first gimbal drive 143A, or a combination thereof, and the like. By way of example, such a range may vary from about 30° in one direction (e.g., tilting forward) to about 20° in the opposite direction (e.g., tilting backward) with respect to the perpendicular axis of the burr hole 182. In similar fashion, an angular range of the second pivotal motion of the IC assembly 150 along the second arcuate path 144B (i.e., the azimuthal angle) may be determined by and/or dependent on a number of factors such as, e.g., at least one of the angle of the threaded shaft of the second gimbal drive relative to the burr hole plane (e.g., angle 402) and a length of the threaded shaft 302B of the second gimbal drive 143B, or a combination thereof, and the like. By way of example, such a range may vary from about 20° in one direction (e.g., tilting left) to about 20° in the opposite direction (e.g., tilting right) with respect to the perpendicular axis of the burr hole 182. It will be realized that the angular ranges set forth herein are purely illustrative and other ranges or combination of ranges may be obtained by appropriately configuring the first and second gimbal drives 143A, 143B, respectively. For example, the first and second gimbal drives 143A and 143B may be configured such that the angular ranges of the first and second pivotal motions are optimized to allow a maximum amount of variability in an entry angle and/or access to the burr hole 182 during a neurological procedure performed on the patient.

Furthermore, the first and second gimbal drives 143A and 143B are independently actuatable, as noted elsewhere in the present patent application, preferably so as to allow maintaining of an entry point on the translational plane (i.e., the burr hole plane 184) that is set after aligning the distal end 197B of the IC assembly 150 using the X-Y slider mechanism of the slider assembly 160 while axial angles of the IC assembly 150 may be changed (i.e., the polar and/or azimuthal angular separation between the longitudinal axis 351 of the IC assembly 150 and the perpendicular axis of the burr hole plane 184) may be varied while the target entry point 183 is held relatively constant or "gimbaled"). It should be apparent that in the exemplary embodiment of the trajectory guiding apparatus 100A, the pivotally rotatable stage 120 is not fixedly attached to the patient's cranium, thus allowing for the pivotal movement of the entire vertical support 130 and the slider assembly 160 attached thereto by the actuation of the first gimbal drive 143A. One skilled in the art will recognize that different gimbal drive arrangements orthogonally disposed to each other may also be implemented according to the teachings herein.

Additionally, because there is no structural supportive framework surrounding or hanging over the frame portion 104 of the base support 102, the trajectory guiding apparatus 100A allows a fairly unhindered access to the burr hole region of the patient's cranium while still providing structural strength by way of the vertical support 130. Accordingly, skilled artisans will appreciate that the "open space" concept of the base support 102 and vertical support 130 arrangement disclosed herein advantageously not only provides geometric stability of the apparatus 100A but also maximizes access to the burr hole 182 to allow intraoperative (i.e., during a procedure) surgical manipulation, as access to the burr hole is critically important for the purposes of, inter alia, attending to any bleeding from the bone cavity, dura, and the surface of the cortex during the procedure, (re)positioning of any implantable medical instrumentation, alignment tools, etc. In a still further aspect, since the slider assembly 160 is removably attached to the vertical support 130, the entire slider assembly 160 may be replaced/removed in an example arrangement to accommodate different types of slider assemblies potentially having different IC assemblies and implantable medical devices according to the application environments, thereby providing further versatility and/or even fuller access to the burr hole region.

As noted previously, shaft 152 of the IC assembly 150 includes columnar passage 198 that may be sized to accommodate a suitable elongate medical device specific to the therapy application. By way of illustration, example medical devices may comprise, without limitation, any type or variety of DBS leads, each comprising a plurality of electrodes at a distal end in a host of configurations (e.g., percutaneous leads, paddle leads, etc. having ring electrodes, segmented electrodes, pad electrodes, and the like), biopsy instrumentation devices, catheter insertion devices, injection and aspiration devices, neurological endoscopy devices, microelectrode recording (MER) devices, macro stimulation devices, cannulas, stylets having a flexible wire (e.g., a guide wire) or similar delivery structures, neurological ablation devices, and brain lesioning devices, and the like, generally referred to herein as "instrumentation" or "implantable medical devices." Whereas at least a portion of the IC assembly 150 or its tubular shaft 152 may form the tapered portion 155 having the distal end 197B facing the burr hole region, a second shaft portion, e.g., portion 153, thereof may be shaped and dimensioned to facilitate the formation of a vertical opening 159 to the internal columnar passage in order to allow a tension member 157 of a drive assembly 154 to frictionally hold the elongate medical device within the columnar passage 198. In one arrangement, the drive assembly 154 may be manually operable to introduce and advance the elongate medical device toward and through the burr hole along a trajectory. In another arrangement, a motorized drive assembly may be provided to automate the advancement of the elongate medical device (e.g., (tele)robotically, based on a suitable medical guided positioning or navigation system in conjunction with bio-imaging/scanning systems). In similar fashion, lower and upper plates 163A/163B actuated by corresponding screw drives 165A/165B as well as the angled gimbal drives 143A/143B may be manually operable by a medical professional to adjust the lateral positioning and/or the angular orientation of the IC assembly 150 during a procedure, i.e., intraoperatively, in order to guide and/or align and the implant trajectory of an elongate medical device. In another arrangement, a motorized drive assembly may be provided to automate the translational and/or pivotal/rotational movement of the elongate medical device (e.g., using (tele)robotics and guided positioning/navigation systems as noted previously). It will be apparent to skilled artisans that the various screw drives as well as the IC drive assembly may be configured to provide both micro adjustments (i.e., adjustments with fine granularity) and macro adjustments (i.e., adjustments with coarse granularity) with respect to any of the axial movement, translational movement or pivotal/rotational movement of the elongate medical device. In one arrangement, any combination of the X-Y slider plates 163A/163B and the angled gimbal drives 143A/143B may be provided with corresponding measurement gauges, scales (e.g., main and/or vernier scales), etc., for providing a visual indication and/or measurement of at least one of a translational movement and a pivotal/rotational movement as the screw drives and/or gimbal drives are manipulated to guide the positioning of the IC assembly 150. Likewise, a portion of either shaft portions 153, 155 of the IC assembly 150 may also be provided with a similar corresponding measurement gauge or scale to provide an indication or measurement of the axial or longitudinal movement of the elongate medical device, which can facilitate a determination of how far the distal end of the elongate medical device has gone in the patient's brain (i.e., a depth measurement). Where screw drives or gear-based drives are employed, the amount of movement, distance, angle or displacement may be varied based on the gear ratios, thread size, etc., provided with the respective mechanical elements, e.g., shafts 404, 604, 302A/B, drive assembly 154, etc., to achieve finer or coarser granular control in the positioning of the IC assembly 150.

In a further example embodiment, a removable burr hole alignment tool 190 may also be optionally employed in association with the base support 102 to facilitate alignment between a burr hole in the patient's cranium and the positioning of an apparatus such as the trajectory guide apparatus 100A. In such an arrangement, the removable burr hole alignment tool 190 may be provided as an annular ring 192 having a handle 194 extending therefrom, wherein the annular ring 192 may be dimensioned and contoured to achieve a snug fit between the burr hole and the aperture 105 of the frame portion 104 when the alignment tool 190 is placed in the burr hole.

Skilled artisans will further recognize that the various structural components and elements of the trajectory guide apparatus 100A set forth herein may be formed, manufactured, assembled, or otherwise fabricated using any known or heretofore unknown technologies (e.g., injection molding, casting, 3D-printing, etc.) involving suitable materials, preferably comprising biocompatible and magnetic resonance imaging (MRI)-compatible materials, such that the trajectory guide apparatus 100A may be deployed in a broad range of therapy applications and settings including where MRI, X-ray, or other radiation-based imaging technologies and systems are used. Accordingly, example non-metallic or non-magnetic materials may include but not limited to thermoplastic polymers, synthetic or semi-synthetic plastics, thermosetting polymers, elastomers, crystalline or non-crystalline amorphous solids, and the like. Components requiring a rigid or firm coupling with other components of the trajectory guide apparatus 100A may be provided with a variety of fastening means 195, 106(N), 164(N), such as, e.g., screws, bolts, pegs, pins, dowels, rivets, binder posts, etc., which may also be formed or fabricated from bio/MRI-compatible materials. Further, whereas various structural elements may be rigidly or semi-rigidly coupled together to form further components or assemblies, it will be understood such components or assemblies may be formed in a unitary construction process such that they form a single structure, preferably of bio/MRI-compatible materials having suitable structural properties. Likewise, various screw drive mechanisms and/or IC drive assembly mechanisms may also be fabricated from similar compatible materials.

Figure 7A:
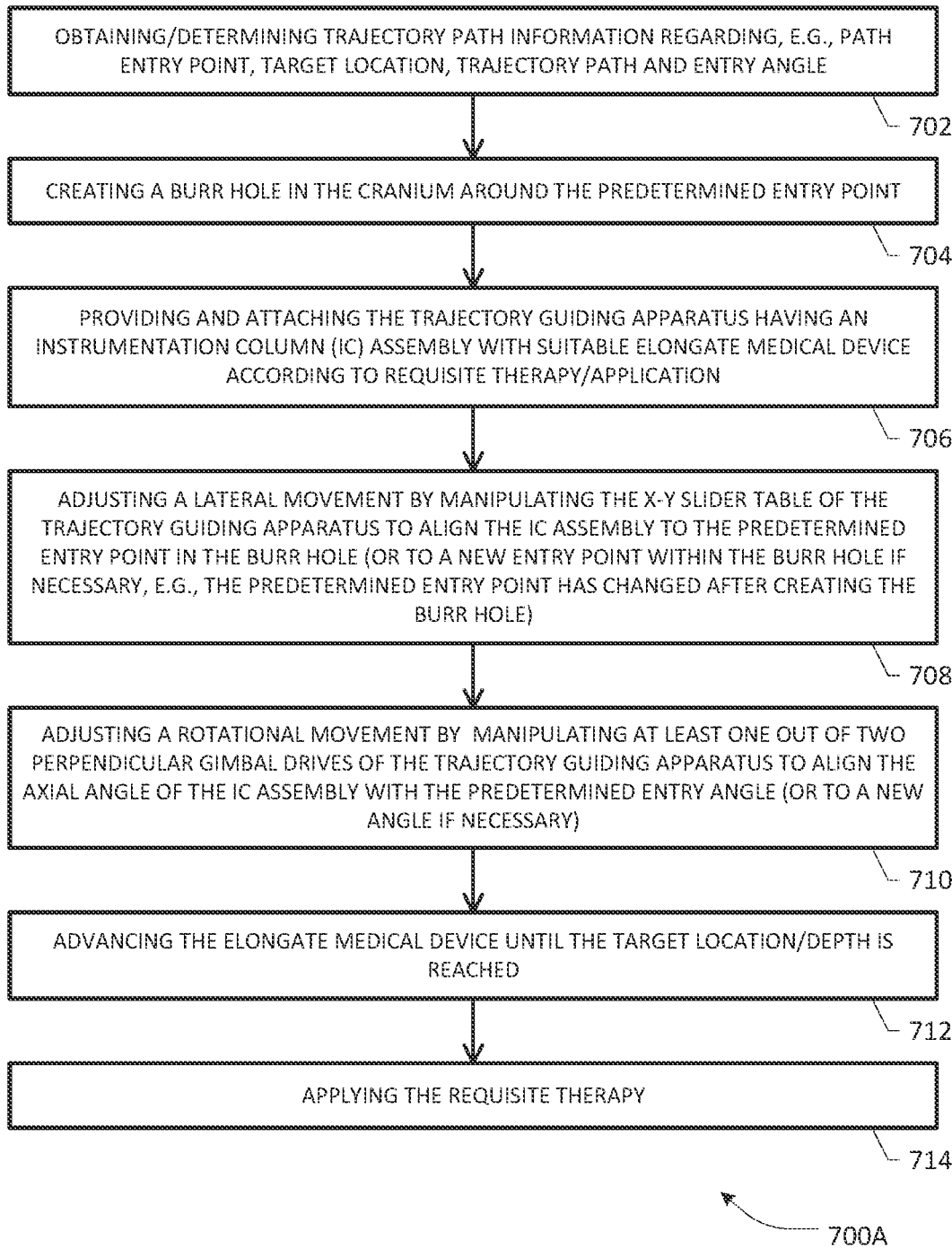
FIGS. 7A and 7B depict flowcharts of various steps, blocks, acts and/or functions that may be combined in one or more (re)arrangements for purposes of practicing a method according to an example embodiment of the present disclosure.
Figure 7B:
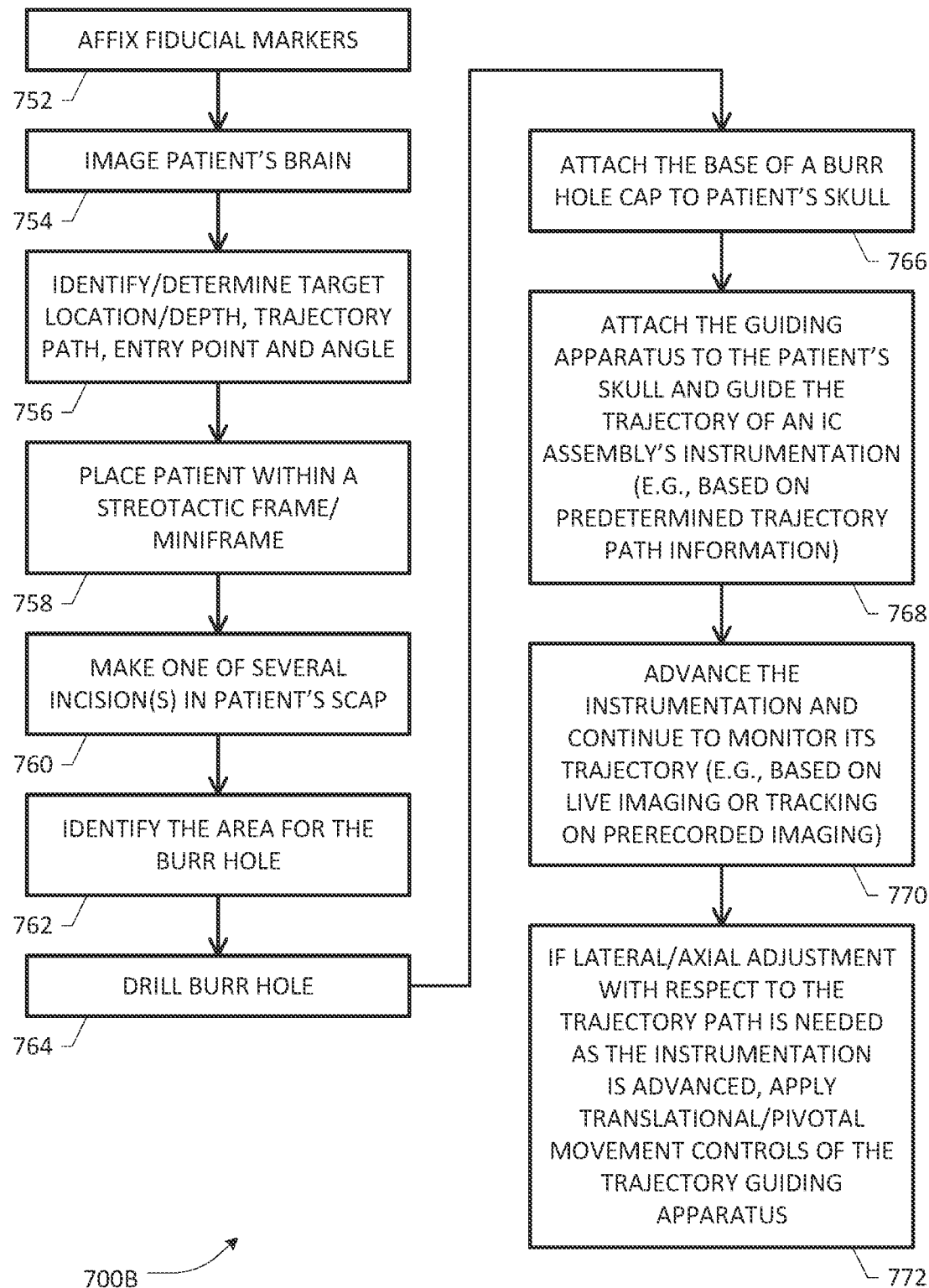

Turning to FIGS. 7A and 7B, depicted therein are flowcharts of various steps, blocks, acts and/or functions that may be combined in one or more (re)arrangements for purposes of practicing an example method according to one or more embodiments of the present disclosure. Process 700A is representative of a methodology or procedure for implanting an elongate medical device into a patient's brain using a trajectory guide apparatus of the present patent disclosure. At block 702, trajectory path information may be determined or otherwise obtained regarding at least one of a path entry point, a target location, a trajectory path and an entry angle with respect to implanting the elongate medical device through the patient's cranium, wherein the elongate medical device is configured to provide a particular therapy. For example, such information may be obtained at least in part based on suitable 2D, 3D or 4D imaging or scanning technologies in reference to the tissue region and the therapy plan being contemplated, e.g., computed tomography (CT) such as 2D/3D X-ray imaging/scanning based on computerized axial tomography (CAT scan), isocentric fluoroscopy, bi-plane fluoroscopy, MRI as well associated 4D imaging (e.g., using movement or flow as the fourth dimension), optical coherence tomography (OCT), planar gamma scintigraphy (PGS), functional imaging techniques such as positron emission tomography (PET), single-photon emission computerized tomography (SPECTscan), functional MRI, magnetic source imaging (MSI) or magnetoencephalography (MEG), or indirectly by using interactive anatomical atlas programs that map a brain atlas image onto the stereotactic image of the brain. Some embodiments may also involve other types of image acquisition technologies such as 3D-transcranial ultrasound (TCU), contrast enhanced TCU, and the like. Various intra-cranial regions or other tissues may be mapped including but not limited to thalamus/sub-thalamus, hippocampus, anterior nucleus, amygdalohippocampal complex, basal ganglia, globus pallidus, cortex or white matter tracts afferent to or efferent from the abovementioned brain tissue, inter alia.

At block 704, one or more burr holes may be drilled based on the trajectory path information around the respective predetermined path entry points in the cranium in accordance with applicable surgical procedures and protocols, depending on how many implantations are contemplated. At block 706, a trajectory guiding apparatus is provided and attached surrounding the burr hole in a close proximity with minimum discomfort to the patient while ensuring firm and secure attachment to the patient's cranium. Skilled artisans will recognize that appropriate care and/or caution may need to be exercised while attaching the guiding apparatus to the cranium, e.g., to avoid drilling into the cranial bone sutures for securing or anchoring a fastener. As previously noted, the trajectory guiding apparatus may be provided with a base support configured to be secured to the cranium and encircle the burr hole as closely as possible, optionally aided by a burr hole alignment tool operative to engage with a base support frame aperture. In one embodiment, it is contemplated that the removable slider assembly portion of the trajectory guide apparatus containing an IC assembly that holds the elongate medical device is securely attached to the lower portion of the apparatus, i.e., the vertical support pivotally engaged the pivotally rotatable stage that is in turn pivotally engaged to the base support, prior to mounting the trajectory guide apparatus to the patient's cranium. In another embodiment, the lower portion comprising the base support may be attached to the patient's cranium first and the upper slider assembly portion of the trajectory guide apparatus may be subsequently mounted thereto (i.e., to the vertical support). At block 708, an X-Y slider table of the trajectory guiding apparatus may be actuated or otherwise manipulated to cause a translational movement adjustment so as to align the IC assembly to the path entry point in the burr hole. If the predetermined entry point has changed or shifted to a new entry point within the burr hole after the burr hole was created, the X-Y slider table may be actuated or otherwise manipulated accordingly to (re)position the IC assembly containing the elongate medical device. Likewise, an axial adjustment (e.g., rotational or pivotal adjustments along one or both arcuate paths) may be caused by actuating or otherwise manipulating at least one of the orthogonally disposed gimbal drives of the trajectory guiding apparatus to align an axial angle of the IC assembly with the entry angle of the predetermined trajectory, which may be (re)aligned as well if needed after creating the burr hole (block 710). Thereafter, the elongate medical device may be advanced using a drive assembly associated with the IC assembly until the target location within the patient's brain is reached (block 712). In one arrangement, an intraoperative guiding and navigation system may be used in aiding the surgeon or an automated entity to monitor and guide the advancement of the elongate medical device along the predetermined trajectory path or a recalibrated trajectory path (e.g., if or when a blood vessel or other structure not previously captured in an image scan or brain atlas is encountered). If a path deviation is determined, at least one of a translational adjustment and a pivotal/rotational adjustment may be applied by actuating or otherwise manipulating at least one of the X-Y slider table and either or both of the gimbal drives to realign the elongate medical device with the (new) trajectory path. Upon reaching the target location within the patient's brain, appropriate therapy (e.g., DBS, laser/radiation treatment, biopsy, catheter placement, drug delivery, neurological ablation or lesioning, etc.) may be applied as set forth at block 714. One skilled in the art will recognize that a variety of bio-imaging/scanning systems (for example such as those referred to hereinabove) may be employed for purposes of intraoperative monitoring and navigation. In a further and/or alternative arrangement, a 3D-navigational system configured to pinpoint device location on pre-recorded X-ray images may also be used for such purposes, thereby advantageously reducing exposure to X-rays during procedures and implants while facilitating intraoperative guidance and device navigation.

Various additional/alternative steps, blocks, acts and/or functions that may be combined in one or more (re)arrangements within the foregoing scheme are set forth as a process 700B shown in FIG. 7B which includes an example burr hole creation procedure. At block 752, fiducial markers or reference points are affixed to the patient's skull. At block 754, imaging of the patient's brain is performed. As noted previously, any suitable imaging technology can be utilized such as MRI systems, CT systems, etc. The imaging may also involve functional analysis of the brain in response to specific stimuli. For example, a functional MRI process may be performed in which stimuli is provided to the patient and the MRI imaging is utilized to identify the specific structures in the brain that respond to the stimuli. At block 756, based upon the imaging information, a target location is identified. Commercially available navigational software can be used to relate the fiducial markers to desired target location. Specifically, the navigational software uses the identified target location with the imaging information of the patient's brain and the fiducial markers to calculate a location for the burr hole and a path for traversal of an implantable medical device to the target location. Preferably, the location of the burr hole and the path are selected to avoid damaging relevant structures of the brain, wherein the trajectory may or may not comprise or follow a single straight path.

At block 758, the patient is placed within a stereotactic frame in a headrest. At block 760, one or more incision(s) may be made on the patient's scalp. At block 762, an identification of the area for the burr hole is made on the patient's skull within the area exposed by the incision(s). At block 764, the burr hole is drilled through the skull. In one example arrangement, a burr hole cap base may be attached to the patient's skull using surgical screws (block 766), which may be used later in order to facilitate attachment of a burr hole cap that is configured to secure and subcutaneously route the implantable medical device for interfacing with external and/or implantable pulse generation (EPG/IPG) circuitry and telemetry apparatus. Additional details regarding an example burr hole cap deployment system for securing a DBS lead may be found in U.S. Pat. No. 7,949,410, entitled "BURR HOLE CAP AND METHODS OF USE", which is incorporated herein by reference. At block 768, a guiding apparatus of the present patent disclosure is attached to the patient's skull to guide the trajectory of an IC assembly's instrumentation (e.g., an elongate implantable medical device) through the brain (e.g., based on predetermined trajectory path information). At block 770, as the instrumentation is advanced, its trajectory may be monitored (e.g., based on tracking on prerecorded imaging or live imaging). If lateral/axial adjustment with respect to the trajectory path is needed as the instrumentation is advanced, appropriate translational/rotational/pivotal movement controls of the trajectory guiding apparatus may be actuated as set forth at block 772.

Figure 8:
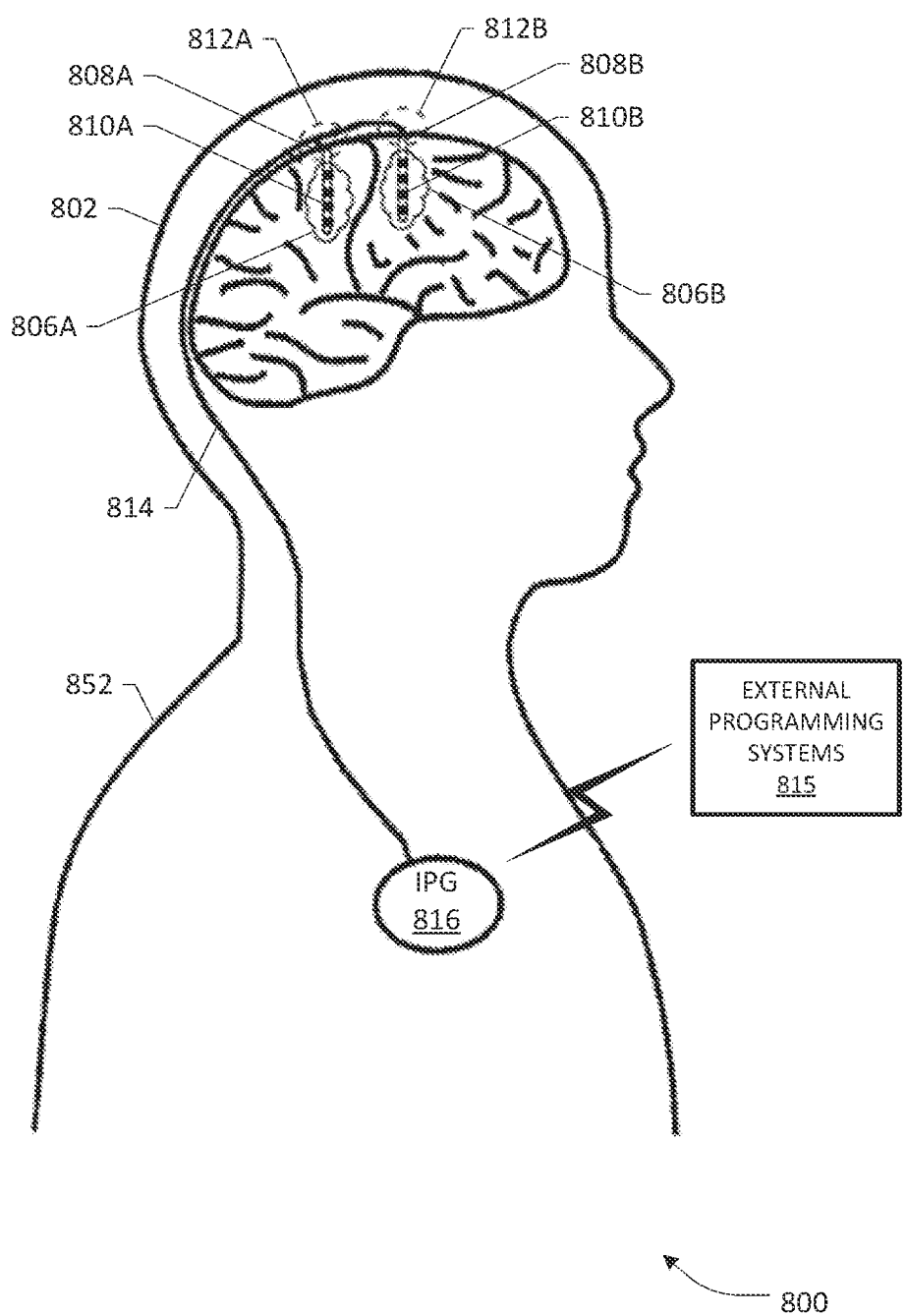
FIG. 8 is an illustrative diagram of a patient having one or more therapy leads implanted in different brain regions using a trajectory guide apparatus of the present disclosure according to the teachings herein.

FIG. 8 is an illustrative diagram of a therapy system 800 exemplifying a patient having one or more therapy leads implanted in different brain regions using a trajectory guide apparatus of the present disclosure according to the teachings herein. By way of illustration, a patient 852 is shown with two regions 806A and 800B of the patient's brain 804 that are implanted with respective DBS leads 808A and 808B, each guided and advanced by the trajectory guide apparatus of the present patent disclosure. Each DBS lead 808A/808B is exemplified as having a respective set of electrodes 810A, 810B. Further details regarding the leads 808A/808B as well as additional and/or alternative embodiments thereof may be found in the following: (i) U.S. Pat. No. 9,370,653, entitled "MEDICAL LEADS WITH SEGMENTED ELECTRODES AND METHODS OF FABRICATION THEREOF"; (ii) U.S. Pat. No. 8,463,387, entitled "STIMULATION OF THE AMYGDALOHIPPOCAMPAL COMPLEX TO TREAT NEUROLOGICAL CONDITIONS"; and (iii) U.S. Patent Application Publication No. 2018/0008821, entitled "IMPLANTABLE THIN FILM DEVICES", each of which is incorporated herein by reference. Respective burr holes 812A and 812B may be drilled in the patient's cranium 802 as described previously based on the desired therapy application, which may be spaced proximate to each other given that the base support 102 and its frame portion 104 of the trajectory guide apparatus 100A is optimized to have a small form factor while providing requisite structural strength to the remaining portions of the trajectory guiding apparatus coupled thereto. After completing the guided implantation of leads 808A/808B, the burr holes 812A and 812B may be capped and secured for routing the leads 808A/808B under the scalp of the patient 852. In one arrangement, electrical traces for the leads 808A/808B may be combined into a single lead body 814 that is routed subcutaneously to be coupled to an implanted pulse generator (IPG) 816, which may be electrically and/or telemetrically coupled to an external programming system 815 to provide appropriate therapy.

Based on the foregoing, skilled artisans will appreciate that embodiments herein provide a trajectory guiding apparatus that can advantageously benefit from a medical guided positioning system configured to provide lead placement trajectories with improved accuracy prior to actual lead implantation insertion without subsequent MRI scanning. Elimination of MRI scans during lead placement eliminates the need for an MRI Operating Room (OR) suite, thereby reducing implantation time and cost, while improving lead placement accuracy (e.g., in the sub-millimeter range in one implementation). When used in conjunction with such a guided positioning/navigation system that provides precise location information of the implantable instrumentation, e.g., the cannula, an embodiment of the present patent disclosure may be configured such that it allows the patients to remain under anesthesia (whereby the patients will not have to endure the pain of securing a tool to their skull). Further, embodiments herein are advantageously configured to minimize the screw size and number of screws used to secure the trajectory guide apparatus, thereby reducing potential discomfort to the patient. In a further variation, the base support of the trajectory guide apparatus may be conformed to the contours of an individual patient's cranium such that a most comfortable fit or attachment may be obtained. Since the base support is removable from the rest of the apparatus, different base supports may be provided for different patients, e.g., as a one-time use option, while the rest of the trajectory guide apparatus may be reused in multiple therapy applications.

In a still further variation, an embodiment of the trajectory guide apparatus may be provided with appropriate mechanical means to insert the instrumentation lead into the patient's brain by use of a direct drive mechanism (e.g., a mechanism that takes the power coming from a motor without any reductions such as a gearbox) for initial insertion and a reduction drive mechanism for precise final implantation positioning. It will be further appreciated that because a removable slider assembly is provided, an embodiment of the trajectory guide apparatus advantageously allows the surgeon to have full access to the burr hole and a tool to ensure alignment between the lower half of the apparatus comprising the gimbal drives and the burr hole.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

Although various embodiments have been shown and described in detail, the claims are not limited to any particular embodiment or example. It will be understood that numerous alterations, variations, modifications, and the like, of the embodiments may be practiced in accordance with the teachings herein. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." Further, "a," "an," "the," "at least one," and "one or more" are used interchangeably herein at least with respect to certain embodiments. Moreover, the terms "first," "second," and "third," etc. employed in reference to elements or features are used merely as labels, and are not intended to impose numerical requirements, sequential ordering or relative degree of significance or importance on their objects. It is noted that the term "comprises" and variations thereof do not have a limiting meaning where these terms appear in the accompanying description and claims. Additionally, relative terms such as "left," "right," "front," "fore," "forward," "rear," "aft," "rearward," "top," "bottom," "side," "upper," "lower," "above," "below," "horizontal," "vertical," and the like may be used herein and, if so, are from the applicable perspective that may be observed with respect to the particular drawing. These terms are used only to simplify the description, however, and not to limit the interpretation of any embodiment described. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method for implanting an elongate medical device into a brain of a patient, the method comprising:
    obtaining trajectory path information regarding a path entry point, a target location, a trajectory path and an entry angle with respect to implanting the elongate medical device through a cranium of the patient, the elongate medical device configured to provide a particular therapy;
    creating a burr hole in the cranium around the path entry point;
    attaching a trajectory guiding apparatus including an instrumentation column (IC) assembly that contains the elongate medical device, the trajectory guiding apparatus having a base support member configured to be secured to the cranium and surround the burr hole in a close proximity;
    adjusting a translational movement of the IC assembly by actuating an X-Y slider table of the trajectory guiding apparatus to align the IC assembly to the path entry point in the burr hole, the X-Y slider table being disposed at a horizontal support member extending from a top of a vertical support;
    adjusting a pivotal rotational movement of the IC assembly by actuating at least one of a first gimbal drive or a second gimbal drive of the trajectory guiding apparatus to align an axial angle of the IC assembly with the entry angle, the first gimbal drive and the second gimbal drive being disposed at a stage portion pivotably coupled to a bottom of the vertical support; and
    advancing the elongate medical device along the trajectory path using a drive assembly associated with the IC assembly until the target location within the brain is reached, wherein the drive assembly is operable to independently actuate the first gimbal drive and the second gimbal drive to maintain alignment of the elongate medical device with the trajectory path.

2. The method as recited in claim 1, further comprising:
    continuing to guide the elongate medical device along the trajectory path as the elongate medical device is advanced in the brain; and
    if a path deviation is determined, applying at least one of a translational adjustment by actuating the X-Y slider table and an axial angular adjustment by actuating at least one of the first gimbal drive and the second gimbal drive to realign the elongate medical device with the trajectory path.

3. The method as recited in claim 2, wherein the elongate medical device comprises at least one of a deep brain stimulation (DBS) lead comprising a plurality of electrodes at a distal end, a biopsy instrumentation device, a catheter insertion device, an injection and aspiration device, a neurological endoscopy device, a microelectrode recording (MER) device, a macro stimulation device, a cannula device, a neurological ablation device, and a brain lesioning device, and further wherein at least one of the first gimbal drive and the second gimbal drive comprises an angled screw drive having a threaded shaft.

4. The method of claim 1, wherein the vertical support is perpendicularly coupled to the stage portion at the bottom.

5. The method of claim 1, wherein the horizontal support member extends perpendicularly from the vertical support.

6. A method for implanting an elongate medical device into a brain of a patient, the method comprising:
    obtaining trajectory path information regarding a path entry point, a target location, a trajectory path and an entry angle with respect to implanting the elongate medical device through a cranium of the patient, the elongate medical device configured to provide a particular therapy;
    creating a burr hole in the cranium around the path entry point;
    attaching a trajectory guiding apparatus including an instrumentation column (IC) assembly that contains the elongate medical device, the trajectory guiding apparatus having a base support member configured to be secured to the cranium and surround the burr hole in a close proximity;
    adjusting a translational movement of the IC assembly by actuating an X-Y slider table of the trajectory guiding apparatus to align the IC assembly to the path entry point in the burr hole;
    adjusting a pivotal rotational movement of the IC assembly by actuating at least one of a first gimbal drive or a second gimbal drive of the trajectory guiding apparatus to align an axial angle of the IC assembly with the entry angle, the first gimbal drive and the second gimbal drive extending horizontally from a stage portion at the base support member; and
    advancing the elongate medical device along the trajectory path using a drive assembly associated with the IC assembly until the target location within the brain is reached, wherein the drive assembly is operable to independently actuate the first gimbal drive and the second gimbal drive to maintain alignment of the elongate medical device with the trajectory path.

7. A method for implanting an elongate medical device into a brain of a patient, the method comprising:
    obtaining trajectory path information regarding a path entry point, a target location, a trajectory path and an entry angle with respect to implanting the elongate medical device through a cranium of the patient, the elongate medical device configured to provide a particular therapy;
    creating a burr hole in the cranium around the path entry point;
    attaching a trajectory guiding apparatus including an instrumentation column (IC) assembly that contains the elongate medical device, the trajectory guiding apparatus having a base support member configured to be secured to the cranium and surround the burr hole in a close proximity;
    adjusting a translational movement of the IC assembly by actuating an X-Y slider table of the trajectory guiding apparatus to align the IC assembly to the path entry point in the burr hole;
    adjusting a pivotal rotational movement of the IC assembly by actuating at least one of a first gimbal drive or a second gimbal drive of the trajectory guiding apparatus to align an axial angle of the IC assembly with the entry angle, the first gimbal drive and the second gimbal drive extending from a stage portion disposed below the X-Y slider table; and advancing the elongate medical device along the trajectory path using a drive assembly associated with the IC assembly until the target location within the brain is reached, wherein the drive assembly is operable to independently actuate the first and second gimbal drives to maintain alignment of the elongate medical device with the trajectory path.

* * * * *

UNITED STATES PATENT AND TRADEMARK OFFICE
CERTIFICATE OF CORRECTION

PATENT NO. : 12,082,978 B2
APPLICATION NO. : 17/688868
DATED : September 10, 2024
INVENTOR(S) : Robert E. Jones et al.

Page 1 of 1

It is certified that error appears in the above-identified patent and that said Letters Patent is hereby corrected as shown below:

In the Specification

At Column 9, Line number 48, delete "(4))" and replace with --($\Phi$)--.
At Column 9, Line number 54, delete "(8)" and replace with --($\theta$)--.

Signed and Sealed this
Fourth Day of February, 2025

Coke Morgan Stewart
*Acting Director of the United States Patent and Trademark Office*